United States Patent [19]
Matsunari

[11] Patent Number: 5,908,411
[45] Date of Patent: Jun. 1, 1999

[54] MOISTURE ANNUNCIATOR

[75] Inventor: Masao Matsunari, Okayama-ken, Japan

[73] Assignee: Nippon Koudoshi Kougyou Co., Ltd., Haruno, Japan

[21] Appl. No.: 08/974,881

[22] Filed: Nov. 20, 1997

[51] Int. Cl.⁶ ...................................................... A61F 13/42
[52] U.S. Cl. ............................................ 604/361; 340/604
[58] Field of Search ............................. 604/361; 340/604

[56] References Cited

U.S. PATENT DOCUMENTS

| | | | |
|---|---|---|---|
| 4,754,264 | 6/1988 | Okada et al. | 604/361 |
| 5,291,181 | 3/1994 | DePonte | 340/604 |
| 5,557,263 | 9/1996 | Fisher et al. | 604/361 |

FOREIGN PATENT DOCUMENTS

| | | |
|---|---|---|
| U-60-181311 | 12/1985 | Japan . |
| Y2-6-7698 | 3/1994 | Japan . |
| Y2-6-21018 | 6/1994 | Japan . |

Primary Examiner—Robert A. Clarke
Assistant Examiner—Catherine Cogut
Attorney, Agent, or Firm—Oliff & Berridge, PLC

[57] ABSTRACT

For a diaper for a baby, a toddler, an old man, or the like, a device for informing a mother of the baby or the toddler or a person who looks after the user of the diaper that the diaper is wet and a sensor for use in the device are provided. A wet annunciator is comprised of: a wet sensor that forms electrostatic capacity between a pair of electrodes 3 and 4 adhesively formed so as to be slightly spaced apart from each other, such that the electrostatic capacity in the vicinity of the electrodes varies when the diaper gets wet; an oscillating device 11 for applying an alternating signal to the electrodes 3 and 4 of the wet sensor; a detector 13 for picking up a change of the electrostatic capacity between the pair of electrodes 3 and 4; and an alerting device such as a vibrator 15, a buzzer or the like, operative according to an output signal of the detector 13. When a diaper is wet due to excretion of the user, the electrostatic capacity between the electrodes 3 and 4 varies, the alerting means is operated, and the mother or the person who looks after the user of the diaper is informed that the diaper gets wet.

18 Claims, 4 Drawing Sheets

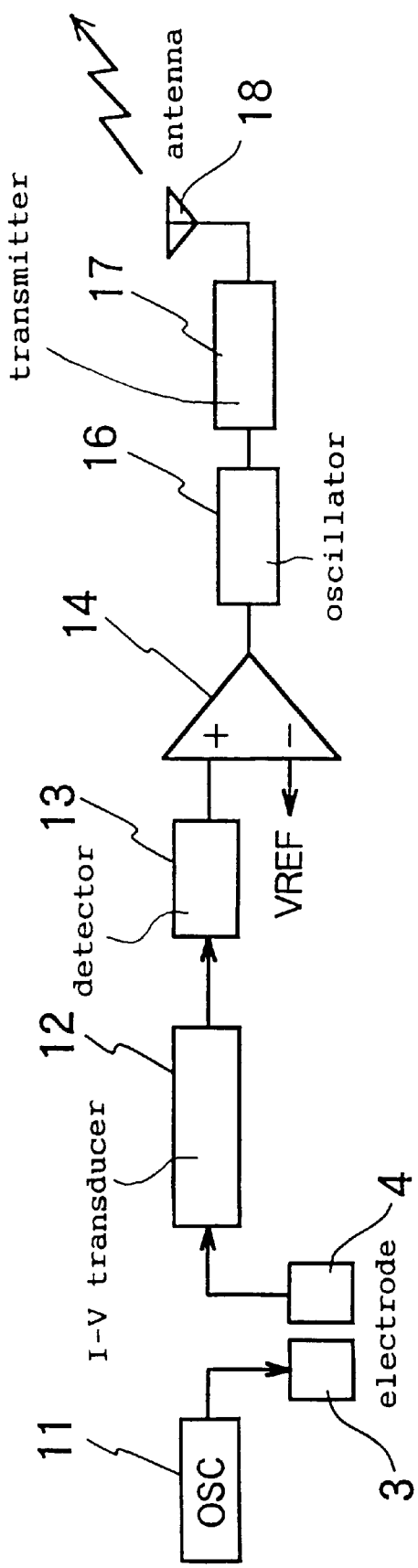
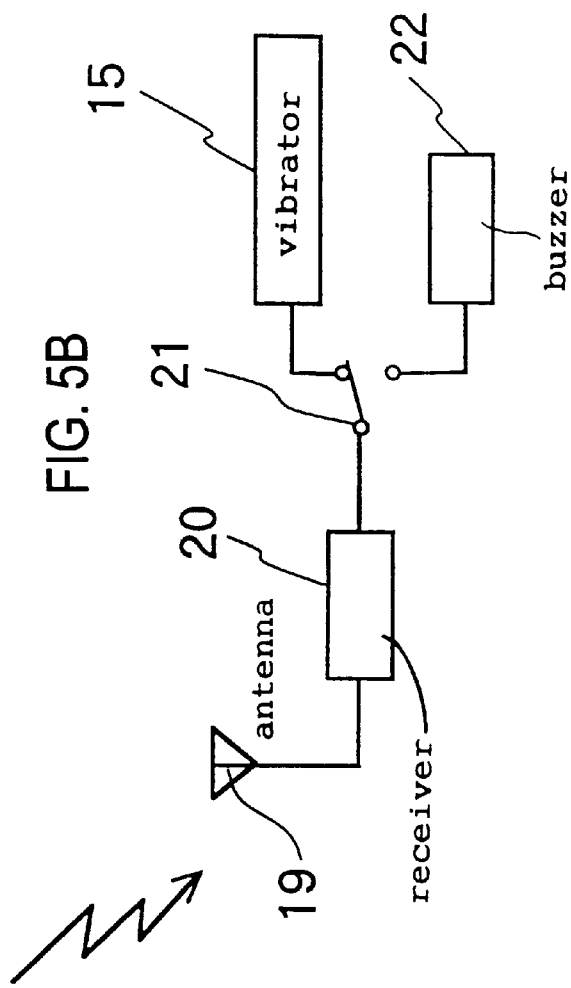
FIG. 5A
FIG. 5B

MOISTURE ANNUNCIATOR

BACKGROUND OF THE INVENTION

1. Field of the Invention

The present invention relates to a wet sensor and a wet annunciator to be used to a diaper (a moisture-generating member) for a baby, a toddler, an old man, or the like.

2. Description of the Related Art

While a diaper (a moisture-generating member) is used normally to a baby or a toddler, the number of old users of diapers is now increasing. A diaper which gets wet due to excretion, if left as it is, may cause uncomfortable odor and skin irritations. Thus, it is ideal that a wet diaper is immediately changed for a new diaper. However, in case a mother takes care of her child, since she changes a diaper for the child according to a sign shown by the child, it is less likely that a wet diaper is left as it is. With regard to a bed-ridden old man in a geriatric hospital and the like, on the other hand, in case a diaper is only changed at a regular interval, especially for the bed-ridden old man, since an excretion interval is different among individuals, the change of the diaper at a regular interval does not meet their requirements. Further, a wet diaper over several excretions being left as it is may occur. It is not preferable for the health and sanitation to leave a wet condition for a long time.

Accordingly, various kinds of devices for electrically detecting a condition that a diaper gets wet and for informing the user or others of the wet condition have been devised. One of them is disclosed in Japanese Utility Model Laid-open No. Sho 60-181311, in which one end portion of a back sheet impermeable to water is extendedly provided so as to cover a water absorbing layer, metal layers are adhesively formed so as to sandwich the portion which is provided extendedly, and, the back sheet and the metal layers, between which the water absorbing layer is sandwiched, form a capacitor, wherein a change of an electrostatic capacity depending on a quantity of adsorbed water in the water absorbing layer is picked up to make known when the diaper gets wet.

Another example is disclosed in Japanese Utility Model Publication No. Hei 6-21018, in which the structure of a sensor for detecting a wet condition mentioned in the above is disclosed specifically. In this example, metal layers are provided in parallel with each other leaving a predetermined space therebetween along the longitudinal direction of a rectangular back sheet impermeable to water. Only one of the metal layers is coated so as to become an electrically insulated layer, and upper surfaces of the two metal layers are coated with a front sheet permeable to water. With this structure, a change of the capacitor formed by the metal layers, the electrically insulated layer, and the front sheet is detected to make known when the diaper gets wet.

Still another example is disclosed in Japanese Utility Model Publication No. Hei 6-7698, in which a moisture sensor with a conductive front surface adsorbing layer is attached to a body of a disposable diaper made of paper, and an output signal of the sensor is sent out to the outside as a radio wave.

These techniques have made it possible to inform a person who looks after the user of the diaper or the like that the diaper gets wet. However, in all of these techniques, since a metal layer is disposed in the diaper, to discard the diaper means to discard the sensor. Accordingly, the sensor may not be used over a long period. It is therefore an object of the present invention to provide a wet annunciator and a wet sensor for use of the wet annunciator which are improved with regard to the point mentioned above.

SUMMARY OF THE INVENTION

According to an invention described herein, a wet annunciator is comprised of: a pair of electrodes disposed separately from each other at a given space; an insulating sheet to prevent the electrodes from being exposed to moisture; an oscillating device for applying an alternating current having a given frequency to the electrodes; a sensor for detecting a change of electrostatic capacity around the electrodes produced by a moisture-generating member disposed adjacent to the space through the insulating sheet; and an alerting means operated by an output signal from the sensor.

According to an invention described herein, a wet annunciator is comprised of: a pair of electrodes disposed separately from each other at a given space; an insulating sheet to prevent the electrodes from being exposed to moisture; an oscillating device for applying an alternating current having a given frequency to the electrodes; a sensor for detecting a change of electrostatic capacity around the electrodes produced by a moisture-generating member disposed adjacent to the space through the insulating sheet; an oscillator for oscillating an output signal from the sensor and an transmitter for sending out the output signal in air as a radio wave; a receiver for receiving the output signal; and an alerting means operated by an output signal from the sensor.

According to an invention described herein, a wet annunciator is comprised of: a pair of electrodes disposed separately from each other at a given space; an insulating sheet to prevent the electrodes from being exposed to moisture; an oscillating device for applying an alternating current having a given frequency to the electrodes; a plurality of sensors for detecting a change of electrostatic capacity around the electrodes produced by a moisture-generating member disposed adjacent to the space through the insulating sheet; an oscillator for applying an ID signal to the output signal of the respective sensors to oscillate it and a transmitter for sending out the output signal in air as a radio wave; a receiver for receiving the output signal; and an alerting means for informing of the respective conditions identified from the ID signal.

According to an invention described herein, in the wet annunciator a vibrator, a buzzer or a display is used as the alerting means.

According to an invention described herein, in the wet annunciator the space formed between the electrodes is configured in parallel to the longitudinal direction of the electrodes, or in bending or winding manner.

According to an invention described herein, in the wet annunciator the moisture-generating member is a diaper.

While a device in the conventional techniques picks up increase of the wet area, a wet sensor structured as above is different from the conventional techniques in that it picks a change of the electrostatic capacity on the wet side with respect to the electrostatic capacity of the side of air, and does not in principle require that the sensor is disposed in the diaper. According to the present invention, the wet annunciator with the wet sensor provides a specific structure which is not shown in the conventional techniques mentioned in the above.

BRIEF DESCRIPTION OF THE DRAWINGS

In the accompanying drawings:

FIGS. 5A and 5B show a circuit diagram of another embodiment of a wet annunciator according to the present invention.

DETAILED DESCRIPTION OF THE PREFERRED EMBODIMENTS

Figure 1:
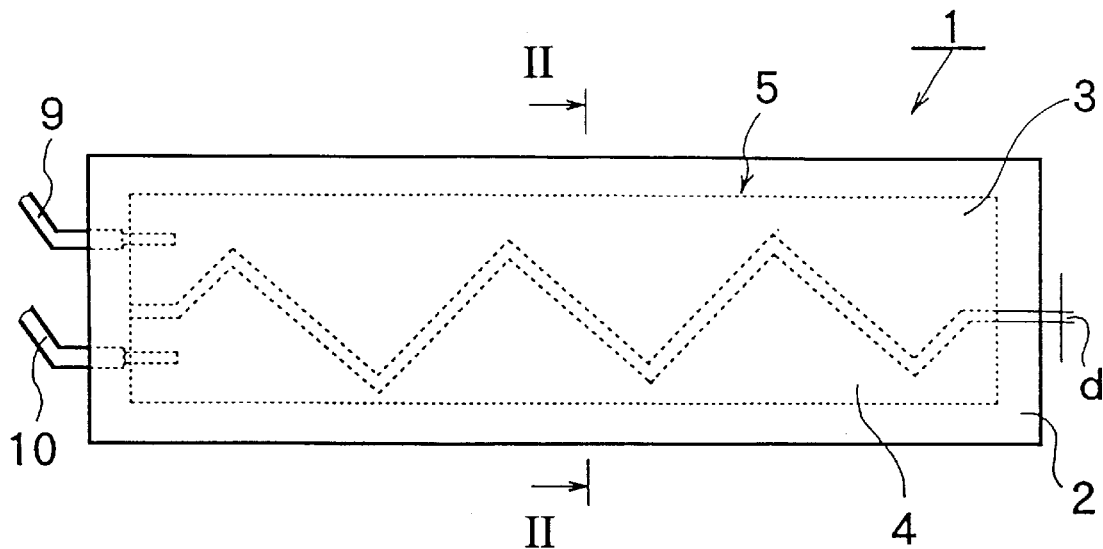
FIG. 1 is a plan view of a wet sensor according to the present invention.
Figure 2:
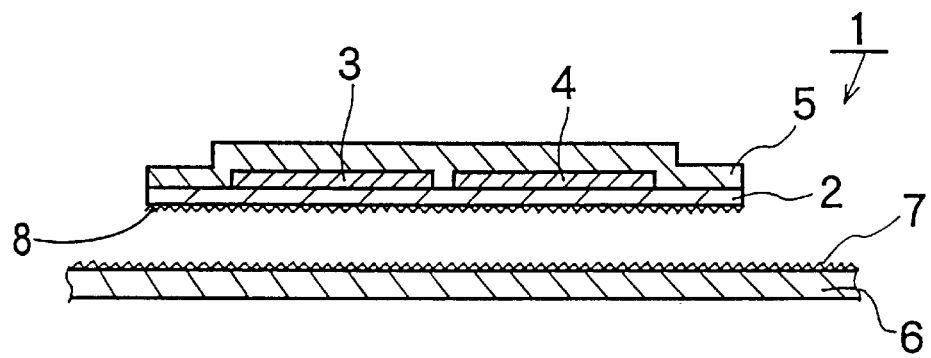
FIG. 2 is a sectional view illustrating the relationship between a sectional view taken along the line A—A of FIG. 1 and a diaper.

Embodiments of the present invention are now described in the following with reference to the drawings. FIGS. 1 and 2 show a wet sensor. The wet sensor 1 is formed by adhesively forming a pair of electrodes 3 and 4 made of metal films so as to be slightly spaced apart from each other (by a distance d) on the upper surface of a back sheet 2 impermeable to water, and then, coating their upper surfaces with a front sheet 5 also impermeable to water.

As shown in FIG. 2, an engaging band 8 for engaging to an engaging band 7 provided on the front surface of a diaper 6 is provided on the back sheet 2. As the engaging bands 7 and 8, preferably, in one engaging band, a fiber is knitted on the front surface thereof to form protruding loops. In the other engaging band, protrusions engaging with the protruding loops are formed on the front surface thereof, but of course, the engaging bands 7 and 8 may be structured otherwise. Lead wires 9 and 10 are connected with the electrodes 3 and 4.

Figure 3:
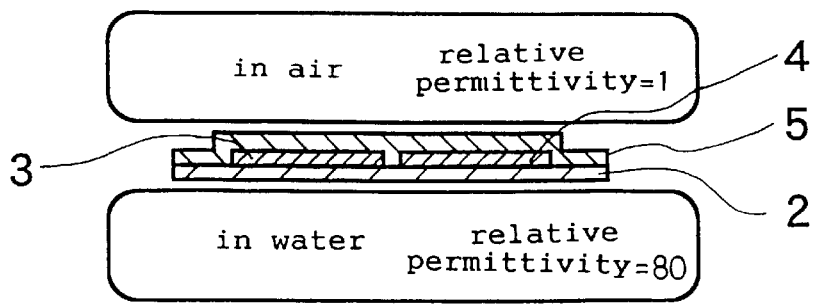
FIG. 3 is an explanatory view explaining the difference between the relative permittivity in air and that in water.

When the back sheet 2 is attached to the front surface of the diaper 6 using the engaging bands 7 and 8, the back sheet 2 is affected by the relative permittivity on the side of the diaper 6, while the front sheet 5 is affected by the relative permittivity in air. FIG. 3 shows a case where the diaper 6 gets wet and the relative permittivity on the side of the back sheet 2 increases to "80" in water. Here, since the relative permittivity on the side of the front sheet 5 remains "1" in air, a great difference is generated therebetween. Accordingly, the electrostatic capacity formed between the electrodes 3 and 4 varies greatly.

As the back sheet 2 and the front sheet 5, rectangular plastic films made of polypropylene, polyester, or the like which is 40 mm or less in width, 80 mm or less in length, and 5–50$\mu$ in thickness were used in the actual manufacturing to collect data. As the electrodes, ones made of aluminum, zinc, copper or the like which are 10–20 mm in width and 50$\mu$ or less in thickness were used. The distance d between the electrodes 3 and 4 was in the order of 0.5 mm. The electrodes 3 and 4 are formed along the longitudinal direction of the back sheet 2 by adhesion, vapor deposition, laminating, or the like. As shown in FIG. 1, the plane of electrodes 3 and 4 are, in plan view, sawtooth with respect to opposing sides, but may be formed in bending shape so as to be corrugated, or simply in parallel with each other. If the electrodes 3 and 4 are sawtooth or corrugated, a complicated shape of the wet portion can be satisfactorily detected.

Figure 4:
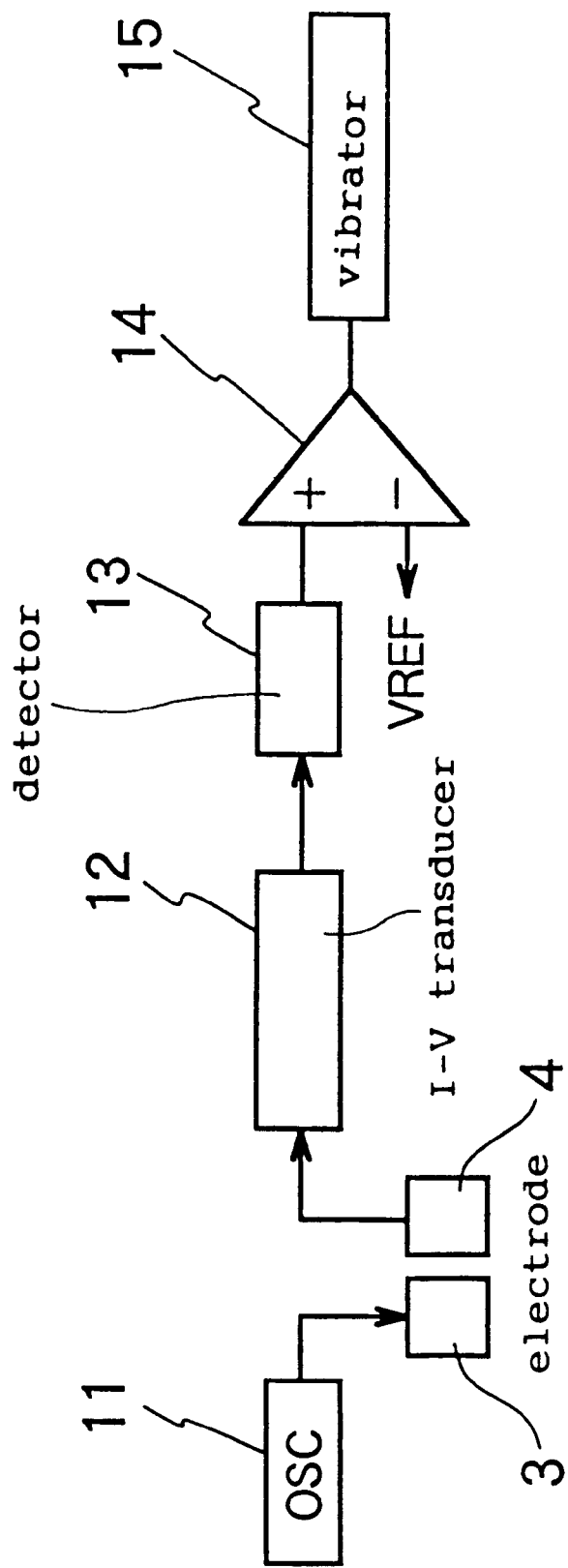
FIG. 4 is a circuit diagram of an embodiment of a wet annunciator according to the present invention.

FIG. 4 shows an embodiment of a wet annunciator using the wet sensor 1. The wet annunciator is now described in the following. An oscillating device 11 applies an alternating signal of a predetermined frequency to the electrode 3 of the wet sensor 1. Since there is electrostatic capacity of a predetermined amount between the electrodes 3 and 4, when an alternating signal is applied to the electrode 3, a voltage is induced to the electrode 4 and the following devices are connected with the electrode 4, electric current according to the electrostatic capacity passes through the electrode 4. That is, a detector 13 is connected with the electrode 4 via an I-V transducer 12 to detect a change of the electrostatic capacity. The resulting signal is supplied via an operational amplifier 14 to a vibrator 15 connected with the output side of the operational amplifier 14.

Effect of the wet annunciator is now described in the following. As described in the above, the wet sensor 1 is used under the condition that the engaging band 8 provided on the back sheet 2 is engaged with the engaging band 7 on the front surface of the diaper 6. In dry condition, since a dryness on the side of the back sheet 2 equals to that on the side of the front sheet 5, a relative permittivity is on the order of "1" on both sides, and no difference is generated. In wet condition, that is, when the diaper 6 gets wet due to excretion of the user, the relative permittivity on the wet side becomes as high as on the order of "80," and thus, the wet condition can be detected immediately.

In this way, on the premise that the wet sensor 1 is attached to the diaper 6, a dry condition and a wet condition are compared. By picking up the great change of the electrostatic capacity due to a change of its condition from dry to wet, the vibrator 15 is operated.

The vibrator 15 is operated in case, for example, an old man who is unconscious of his excretion can dispose of it if he is informed of it. In case a person can not dispose of the excretion himself and thus depends on other people, instead of or in addition to the vibrator 15, a buzzer may be connected.

FIGS. 5A and 5B show another embodiment of the present invention. The circuit comprises an oscillator 16 for modulating an output signal of a detector 13, a transmitter 17 for sending out the signal in air, an antenna 18, an antenna 19 for receiving a radio wave from the antenna 18, a receiver 20 for receiving and detecting the radio wave from the antenna 19, a selector switch 21 for switching an output signal of the receiver 20, and a vibrator 15 and a buzzer 22 connected with the selector switch 21.

In this embodiment, when the electrostatic capacity between the electrodes 3 and 4 varies due to the wet condition of the diaper 6, that signal is sent as a radio wave to the receiver 20 to operate the vibrator 15 or the buzzer 22 selected by the selector switch 21. If the vibrator 15 is selected, a person who carries the vibrator 15 with him or who looks after the user of the diaper is informed of the situation by the vibration. If the buzzer 22 is selected, the situation is known by the sound. Therefore, a person who looks after the user of the diaper can immediately change the diaper 6.

Figure 6A:
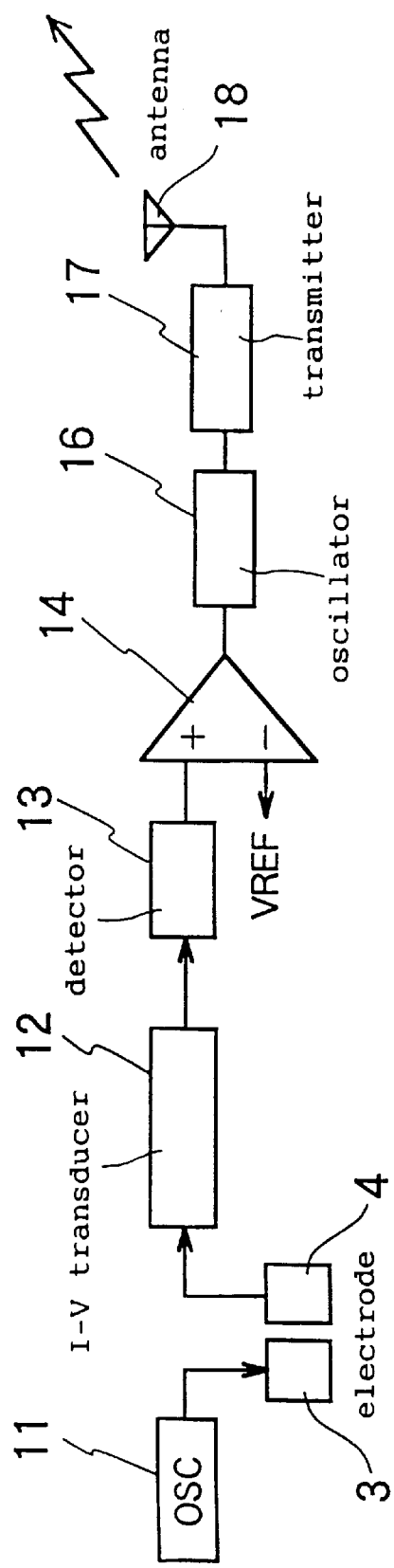
FIGS. 6A and 6B show a circuit diagram of still another embodiment of a wet annunciator according to the present invention.
Figure 6B:
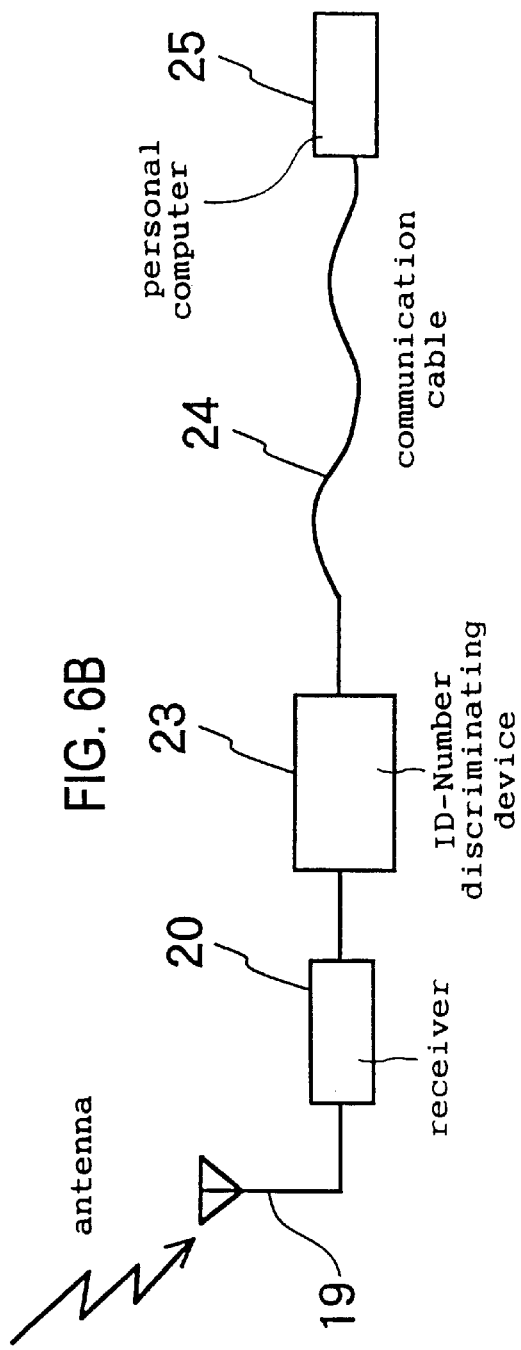

FIGS. 6A and 6B show still another embodiment of the present invention. In this embodiment, an oscillator 16 has a function to allot ID numbers, and an ID number discriminating device 23 is provided in the stage subsequent to a receiver 20. The output side of the ID number discriminating device 23 is connected via communication cable 24 to, for example, a personal computer 25.

In this embodiment, since individuals can be discriminated by their ID numbers, conditions of a plurality of users can be monitored at the same time. More specifically, when the electrostatic capacity between electrodes 3 and 4 varies due to the wet condition of the diaper, an ID number is allotted to a signal informing the above condition by the oscillator 16, and the signal is sent out in air as a radio wave. The receiver 20 receives the radio wave via an antenna 19, inputs a detected output to the ID number discriminating device 23, and, by the ID number, the person whose diaper gets wet is known from the display of the personal computer 25.

In the embodiment shown in FIGS. 6A and 6B, the ID number discriminating device 23 and the personal computer 25 are connected via the communication cable 24. However, the two may be in radio-communication with each other by a radio wave. Further, the personal computer 25 may be replaced by a larger computer, or by a microcomputer with a specific function.

In the embodiment recited in the above, as a member under the influence of humidity, "a diaper" is introduced. Other than the diaper, the device of the present invention has a large variety of usage, as far as the member is used under the influence of humidity and a wet condition needs to be detected. For example, the device of the present invention may be used to a detector for detecting a perspiration of a patient, a water level of bath and the like.

According to the present invention, since a wet annunciator and a wet sensor are structured as described in the above, when a diaper gets wet, the user of the diaper or a person who looks after the user can be immediately informed of the wet condition. The present invention also has an advantage that, since the wet detecting sensor can be attached to the outside of a diaper and the electrodes of the sensor are not required to get wet, the sensor can be repeatedly used.

What is claimed is:

1. A moisture annunciator comprising:
   a pair of electrodes disposed separately from each other at a given space;
   a moisture insulating sheet which covers the electrodes so as to prevent the electrodes from being exposed to moisture;
   an oscillating device for applying an alternating current having a given frequency to the electrodes;
   a detector for detecting a change of electrostatic capacity around the electrodes caused by moisture in a member disposed adjacent to the given space; and
   an alerting means operated by an output signal from the detector for indicating a change of moisture condition of the member.

2. The moisture annunciator of claim 1, wherein the alerting means comprises a vibrator, a buzzer or a display.

3. The moisture annunciator of the claim 2, wherein the space formed between the electrodes is parallel to a longitudinal direction of the electrodes, or has a non-linear configuration in the longitudinal direction of the electrodes.

4. The moisture annunciator of the claim 2, wherein the member is a diaper.

5. The moisture annunciator of claim 1, wherein the space formed between the electrodes is parallel to a longitudinal direction of the electrodes, or has a non-linear configuration in the longitudinal direction of the electrodes.

6. The moisture annunciator of the claim 5, wherein the member is a diaper.

7. The wet annunciator of the claims 1, wherein the member is a diaper.

8. A moisture annunciator comprising:
   a pair of electrodes disposed separately from each other at a given space;
   a moisture insulating sheet which covers the electrodes so as to prevent the electrodes from being exposed to moisture;
   an oscillating device for applying an alternating current having a given frequency to the electrodes;
   a detector for detecting a change of electrostatic capacity around the electrodes caused by moisture in a member disposed adjacent to the given space;
   an oscillator for oscillating an output signal from the detector and a transmitter for sending out the output signal in air as a radio wave;
   a receiver for receiving the output signal; and
   an alerting means operated by an output signal from the receiver for indicating a change of moisture condition of the member.

9. The moisture annunciator of claim 8, wherein the alerting means comprises a vibrator, a buzzer or a display.

10. The moisture annunciator of the claim 8, wherein the space formed between the electrodes is parallel to a longitudinal direction of the electrodes, or has a non-linear configuration in the longitudinal direction of the electrodes.

11. The moisture annunciator of the claim 8, wherein the member is a diaper.

12. A moisture annunciator comprising:
    at least one pair of electrodes disposed separately from each other at a given space;
    a moisture insulating sheet which covers each of the at least one pair of electrodes so as to prevent the pair of electrodes from being exposed to moisture;
    an oscillating device for applying an alternating current having a given frequency to the at least one pair of electrodes;
    at least one detector for detecting a change of electrostatic capacity around the at least one pair of the electrodes caused by moisture in a member disposed adjacent to the space;
    an oscillator for applying an ID signal to an output signal of the at least one detector to oscillate the output signal and a transmitter for sending out the output signal in air as a radio wave;
    a receiver for receiving the output signal; and
    an alerting means for informing of the condition identified from the ID signal.

13. The moisture annunciator of claim 12, wherein the alerting means comprises a vibrator, a buzzer or a display.

14. The moisture annunciator of the claim 12, wherein the space formed between the at least one pair of electrodes is parallel to a longitudinal direction of the at least one pair of electrodes, or has a non-linear configuration in the longitudinal direction of the at least one pair of electrodes.

15. The moisture annunciator of the claim 12, wherein the member is a diaper.

16. A moisture annunciator for use with a member that can contain moisture, the moisture annunciator comprising:
    a pair of electrodes separated from each other by a space;
    a moisture impermeable sheet covering the electrodes so as to prevent the electrodes from being exposed to moisture, the moisture impermeable sheet being removably positionable relative to the member such that the member is adjacent to the space;
    an oscillating device that applies an alternating current having a frequency to the electrodes;
    a detector that detects a change of electrostatic capacity around the electrodes caused by moisture contained in the member disposed adjacent to the space; and a device operated by an output signal from the detector that indicates a change of moisture condition of the member.

17. The moisture annunciator of claim 16, further comprising an element on the moisture impermeable sheet that is removably attachable to a mating element of the member.

18. In combination:
   a diaper that can be worn by an individual, the diaper having an inner surface that faces the individual and an outer surface that faces away from the individual, when the diaper is being worn; and
   a reusable moisture annunciator, comprising:
      a pair of electrodes separated from each other by a space;
      a moisture impermeable sheet covering the electrodes so as to prevent the electrodes from being exposed to moisture, the moisture impermeable sheet being removably attachable to the outer surface of the diaper such that the diaper is adjacent to the space;
      an oscillating device that applies an alternating current having a frequency to the electrodes;
      a detector that detects a change of electrostatic capacity around the electrodes caused by moisture contained in the diaper disposed adjacent to the space; and
      a device operated by an output signal from the detector that indicates a change of moisture condition of the diaper.

\* \* \* \* \*